United States Patent
Mimitsuka et al.

(10) Patent No.: US 10,093,948 B2
(45) Date of Patent: Oct. 9, 2018

(54) METHOD OF PRODUCING ALCOHOL FROM CELLULOSE-CONTAINING BIOMASS

(71) Applicant: Toray Industries, Inc., Tokyo (JP)

(72) Inventors: Takashi Mimitsuka, Kamakura (JP); Katsushige Yamada, Kamakura (JP); Kenji Sawai, Kamakura (JP); Koji Kobayashi, Kamakura (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 14/904,449

(22) PCT Filed: Jul. 10, 2014

(86) PCT No.: PCT/JP2014/068385
§ 371 (c)(1),
(2) Date: Jan. 12, 2016

(87) PCT Pub. No.: WO2015/005410
PCT Pub. Date: Jan. 15, 2015

(65) Prior Publication Data
US 2016/0160242 A1    Jun. 9, 2016

(30) Foreign Application Priority Data

Jul. 12, 2013   (JP) ................. 2013-146486

(51) Int. Cl.
*C12P 7/04* (2006.01)
*C12P 7/10* (2006.01)
*C12P 7/16* (2006.01)

(52) U.S. Cl.
CPC .................. *C12P 7/16* (2013.01); *C12P 7/04* (2013.01); *C12P 7/10* (2013.01); *C12P 2203/00* (2013.01); *Y02E 50/10* (2013.01); *Y02E 50/16* (2013.01)

(58) Field of Classification Search
None
See application file for complete search history.

(56) References Cited

U.S. PATENT DOCUMENTS

2009/0269812 A1   10/2009   Sawai et al.
2011/0250637 A1   10/2011   Kurihara et al.

FOREIGN PATENT DOCUMENTS

| EP | 2 371 973 | 10/2011 |
|---|---|---|
| EP | 2 612 920 | 7/2013 |
| FR | 2 974 311 | 10/2012 |
| JP | 2009-184894 A | 8/2009 |
| JP | 2009184894 A * | 8/2009 |
| JP | WO 2011115039 A1 * | 9/2011 |
| JP | 2013-13388 A | 1/2013 |
| JP | 2013-59284 A | 4/2013 |
| WO | 2007/097260 A1 | 8/2007 |
| WO | 2008/025522 | 3/2008 |
| WO | 2010/067785 A1 | 6/2010 |

OTHER PUBLICATIONS

D. Humbird et al., "Process Design and Economics for Biochemical Conversion of Lignocellulosic Biomass to Ethanol", NREL Report No. TP-5100-47764, May 2011.
M. Furuichi, "Utilization of membrane separation techniques in alcohol manufacturing process from biomass", *Bioscience & Industry*, Sep. 1, 1989, vol. 47, No. 9, pp. 951-954.
Decision to Grant a Patent dated May 8, 2015 of related Japanese Patent Application No. 2014-552419 along with an English translation.
European Search Report dated Feb. 21, 2017, from corresponding European Application No. 14822174.0.
Dias, M.O.S et al.: "Production of Bioethanol and Other Bio-Based Materials from Sugarcane Bagasse: Integration to Conventional Bioethanol Production Process," *Chemical Engineering Research and Design*, 2009, vol. 87, No. 9, pp. 1206-1216.
Australian Examination Report No. 1 dated Mar. 14, 2017, of corresponding Australian Application No. 2014288229.

* cited by examiner

*Primary Examiner* — Michelle F. Paguio Frising
(74) *Attorney, Agent, or Firm* — DLA Piper LLP (US)

(57) ABSTRACT

A method of producing alcohol from cellulose-containing biomass includes steps (1) to (8): step (1): pretreating a cellulose-containing biomass; step (2): saccharifying the pretreated cellulose-containing biomass obtained in step (1) with a saccharification enzyme; step (3): removing a saccharification residual solid from a saccharification treated product obtained in step (2); step (4): culturing an alcohol fermentation microorganism with an aqueous sugar solution obtained in step (3) as a fermentation raw material; step (5): removing the alcohol fermentation microorganism from a culture liquid containing the alcohol fermentation microorganism obtained in step (4); step (6): distilling the alcohol fermentation liquid obtained in step (5) to recover alcohol; step (7): passing and filtering a distillation residual liquid obtained in step (6) through a reverse osmosis membrane; and step (8): performing treatment of discharging a retentate obtained in step (7).

21 Claims, 6 Drawing Sheets

METHOD OF PRODUCING ALCOHOL FROM CELLULOSE-CONTAINING BIOMASS

TECHNICAL FIELD

This disclosure relates to a method of producing alcohol from cellulose-containing biomass.

BACKGROUND

In recent years, attention has been given to technologies that produce bioethanol by fermentation, as technologies that can reduce the consumptions of oil resources and the amount of carbon dioxide emissions to produce fuel and industrial materials which are sustainable against the backdrop of increases in global environmental awareness over the whole world, steep rises in crude oil prices and the like.

However, increases in production of biofuel from food grain (for example, corn, tubers and roots, sugar cane or the like) have caused steep rises in food prices, and production of ethanol from cellulose-containing biomass (for example, herbaceous biomass such as bagasse, switchgrass, corn stover, rice straw, or wheat straw; or wood-based biomass such as trees or waste building materials) has become an important technological development.

As a method of producing alcohol from cellulose-containing biomass, a method of producing ethanol from cellulose-containing biomass is disclosed in a technological report (D. Humbird et al., "Process Design and Economics for Biochemical Conversion of Lignocellulosic Biomass to Ethanol", NREL Report No. TP-5100-47764, May 2011) of NREL (National Renewable Energy Laboratory).

In the method disclosed in D. Humbird et al., "Process Design and Economics for Biochemical Conversion of Lignocellulosic Biomass to Ethanol", NREL Report No. TP-5100-47764, May (2011), cellulose-containing biomass is first subjected to pretreatment using water vapor, acid or alkali (pretreatment step) to facilitate treatment of saccharification enzyme in a subsequent step. The cellulose-containing biomass subjected to the pretreatment is then supplied to a saccharification/fermentation tank, a saccharification enzyme (for example, cellulase or the like) and a nutrient are added to the saccharification/fermentation tank, which is then inoculated with ethanol fermentation bacteria to simultaneously perform saccharification and fermentation (saccharification step and fermentation step). As a result, a fermentation liquid is obtained. The fermentation liquid contains saccharification residual solids (most of which are lignin and the like), ethanol fermentation bacteria and the like. Thus, the obtained fermentation liquid is distilled to purify and recover ethanol (distillation step). The saccharification step and the fermentation step are simultaneously performed in the method, to therefore enable the number of necessary tanks to be reduced, and a capital investment can be therefore reduced so that the method is considered to be a competitive method.

In another method of producing alcohol from cellulose-containing biomass, an aqueous sugar solution obtained by hydrolyzing cellulose-containing biomass is filtered to remove a fermentation inhibitor contained in the aqueous sugar solution, followed by using the purified aqueous sugar solution to enable ethanol fermentation (WO 2010/067785).

In such a method of producing alcohol from cellulose-containing biomass as in D. Humbird et al., "Process Design and Economics for Biochemical Conversion of Lignocellulosic Biomass to Ethanol", NREL Report No. TP-5100-47764, May (2011) mentioned above, the concentration of ethanol obtained in the fermentation step depends on the amount of cellulose-containing biomass that can be put in a saccharification/fermentation tank. Therefore, the amount of cellulose-containing biomass that can be supplied into the saccharification/fermentation tank precludes the concentration of ethanol obtained in the fermentation step from being, for example, 5.5 wt % or more so that a large amount of distillation residual liquid generated after a distillation step (for example, about 17 times greater than the amount of produced ethanol) is generated to cause the large load of treatment of discharging the distillation residual liquid.

In such a method of producing alcohol from cellulose-containing biomass as in WO 2010/067785, an ethanol fermentation liquid can be obtained from an aqueous sugar solution. However, further improvement of treatment of a distillation residual liquid generated when an obtained ethanol fermentation liquid is distilled to recover ethanol is also required to further improve a method of producing ethanol.

In other words, a method of producing alcohol with the reduced amount of liquid discharged when alcohol is produced from cellulose-containing biomass is demanded, and a problem is to reduce the load of treatment of liquid discharged when a distillation residual liquid is treated.

Thus, it could be helpful to provide a method of producing alcohol from cellulose-containing biomass in which the amount of discharged liquid necessary to treat the discharged liquid when alcohol is produced from cellulose-containing biomass can be greatly reduced.

SUMMARY

We found that a step of removing a saccharification residual solid contained in a saccharification treated product obtained by hydrolyzing cellulose-containing biomass and a step of removing an alcohol fermentation microorganism from a culture liquid containing the alcohol fermentation microorganism obtained with an aqueous sugar solution contained in the saccharification treated product as a fermentation raw material are performed in adequate stages, respectively, in production of alcohol from cellulose-containing biomass. By performing the above two steps in adequate stages, respectively, a distillation residual liquid generated after a distillation step can be treated through a reverse osmosis membrane. Thus, the amount of liquid discharged when the alcohol is produced can be greatly reduced.

We thus provide:

[1] A method of producing alcohol from cellulose-containing biomass, the method comprising the following steps (1) to (8):

step (1): the step of pretreating a cellulose-containing biomass;

step (2): the step of saccharifying the pretreated cellulose-containing biomass obtained in step (1) with a saccharification enzyme;

step (3): the step of removing a saccharification residual solid from a saccharification treated product obtained in step (2);

step (4): the step of culturing an alcohol fermentation microorganism with an aqueous sugar solution obtained in step (3) as a fermentation raw material;

step (5): the step of removing the alcohol fermentation microorganism from a culture liquid containing the alcohol fermentation microorganism obtained in step (4);

step (6): the step of distilling the alcohol fermentation liquid obtained in step (5) to recover alcohol;

step (7): the step of passing and filtering a distillation residual liquid obtained in step (6) through a reverse osmosis membrane; and step (8): the step of performing treatment of discharging a retentate obtained in step (7).

[2] The method of producing alcohol from cellulose-containing biomass according to [1], wherein step (5) is a step of passing and filtering the culture liquid containing the alcohol fermentation microorganism obtained in step (4) through a microfiltration membrane.

[3] The method of producing alcohol from cellulose-containing biomass according to [1] or [2], wherein step (3) is a step using a filter press.

[4] The method of producing alcohol from cellulose-containing biomass according to any one of claims [1] to [3], wherein a permeate obtained through the reverse osmosis membrane in step (7) is reused as process water for step (1), (2), or (4).

[5] The method of producing alcohol from cellulose-containing biomass according to any one of [1] to [4], wherein step (7) is a step of directly passing and filtering the distillation residual liquid obtained in step (6) through the reverse osmosis membrane.

[6] The method of producing alcohol from cellulose-containing biomass according to any one of claims [1] to [5], wherein the alcohol is methanol, ethanol, propanol, or butanol.

The saccharification residual solid in the saccharification treated product is removed in advance in step (3) before the saccharification treated product of the cellulose-containing biomass obtained in step (2) is fermented in step (4), and the alcohol fermentation microorganism in the culture liquid is removed in advance in step (5) before the culture liquid containing the alcohol fermentation liquid obtained in step (4) is distilled in step (6), to obtain an alcohol fermentation liquid with the small amount of impurities. As a result, the residual liquid obtained after the distillation step in the production of alcohol can be passed through the reverse osmosis membrane, and therefore, the amount of discharged liquid needed for being supplied to the discharge treatment step can be greatly reduced.

DETAILED DESCRIPTION

Our methods will be described in detail below. The methods are not limited to the examples described below.

Method of Producing Alcohol from Cellulose-Containing Biomass

Figure 1:
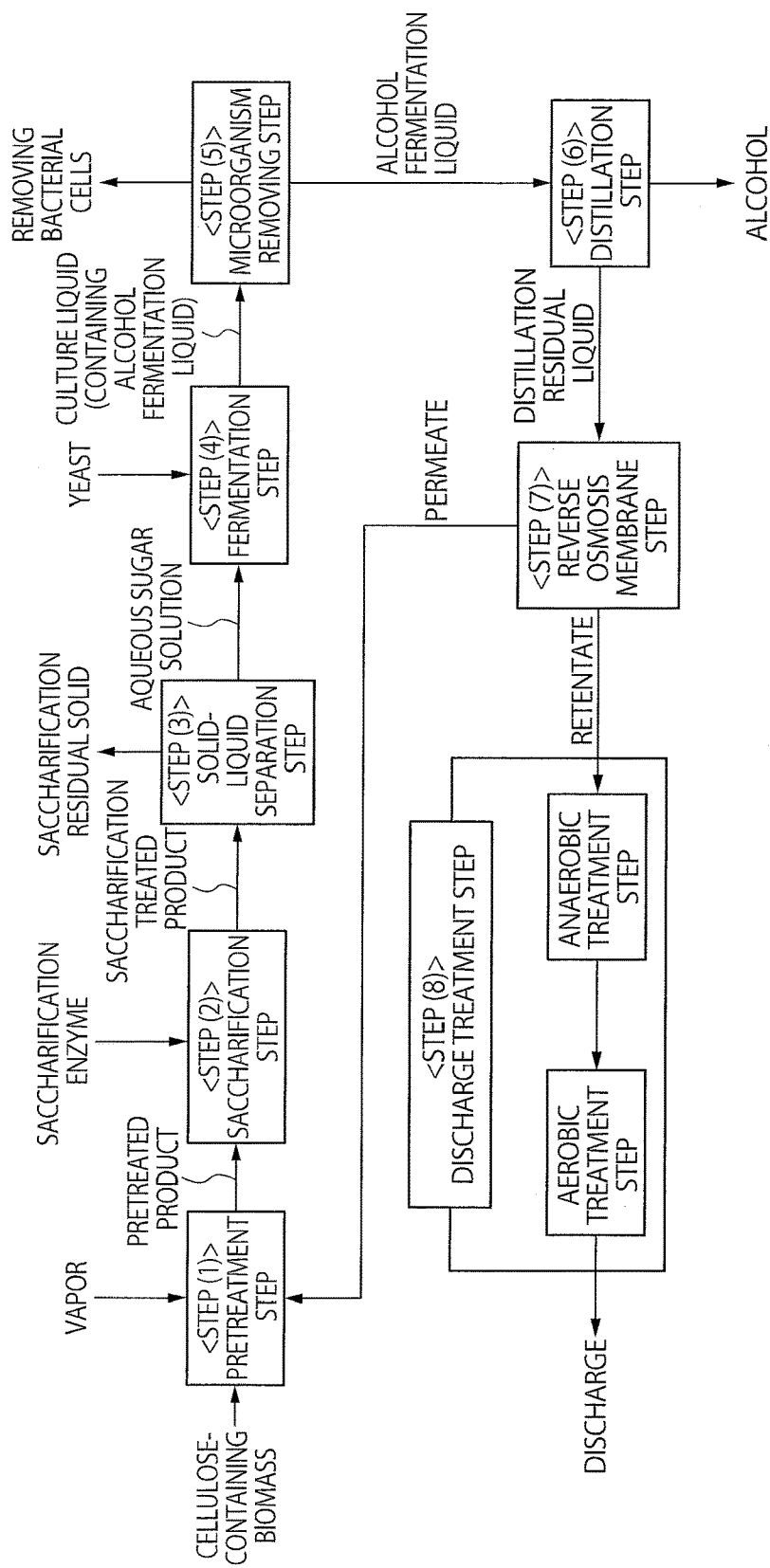
FIG. 1 is a drawing showing a flow of the steps of producing alcohol from cellulose-containing biomass.

A method of producing alcohol from cellulose-containing biomass is shown in FIG. 1. The method of producing alcohol from cellulose-containing biomass (hereinafter may be simply referred to as a method of producing alcohol) will be described for each step.

As used herein, alcohol is not particularly restricted as long as it is alcohol produced from a sugar by microorganism fermentation and is isolated and purified in a distillation step. Specific examples thereof include methanol, ethanol, propanol, butanol or the like. The propanol may be 1-propanol or 2-propanol. The butanol may be 1-butanol, 2-methyl-1-propanol, 2-butanol, or 2-methyl-2-propanol.

Cellulose-containing biomass refers to a natural resource containing a cellulose component. Specific examples thereof may include herbaceous biomass such as bagasse, switchgrass, napier grass, *Erianthus*, corn stover, beet pulp, cottonseed hulls, palm empty fruit bunch, rice straw, wheat straw, bamboo, or bamboo grass; trees such as white birch and beech; wood-based biomass such as waste building materials; biomass derived from aquatic environment such as algae or seaweeds and the like. Such cellulose-containing biomass contains cellulose or hemicellulose which is a polysaccharide formed by dehydration condensation of sugars, and can be used as a fermentation raw material by hydrolyzing such a polysaccharide.

In general, sugars are classified according to the polymerization degree of monosaccharides; and classified into monosaccharides such as glucose and xylose, oligosaccharides each formed by dehydration condensation of two to nine monosaccharides, and polysaccharides formed by dehydration condensation of 10 or more monosaccharides.

Step (1): Pretreatment Step

In step (1), cellulose-containing biomass is pretreated to obtain a pretreated product. The efficiency of hydrolysis of the cellulose-containing biomass can be improved by pretreating in advance the cellulose-containing biomass before the cellulose-containing biomass is treated in a saccharification step mentioned later. As a method of pretreating the cellulose-containing biomass, which is not particularly limited, any conventionally known pretreatment method can be used. Examples of the pretreatment method include fine grinding treatment, hydrothermal treatment, ammonia treatment, alkali treatment, acid treatment, sulfate treatment, dilute sulfuric acid treatment, acetic acid treatment, caustic soda treatment, blasting treatment, subcritical water treatment, digestive treatment and the like, of which any may be used, or which may be used in combination.

Step (2): Saccharification Step

In step (2), the pretreated product obtained in step (1) is hydrolyzed into monosaccharides or oligosaccharides each formed by dehydration condensation of two to nine monosaccharides. As a result, a saccharification treated product is obtained. A saccharification enzyme is preferably used for hydrolyzing the pretreated product.

Reaction conditions for hydrolysis with a saccharification enzyme may conform to the preferred reaction conditions of the saccharification enzyme. A pH for a hydrolysis reaction is preferably 3 to 7, more preferably 4 to 5.5, and further preferably a pH of around 5. The reaction temperature is preferably 40 to 70° C., and more preferably around 50° C.

To homogenize the concentration of a sugar in the saccharification treated product while promoting contact between the pretreated product and the saccharification enzyme, the pretreated product and the saccharification enzyme are preferably mixed while being stirred.

The saccharification enzyme refers to an enzyme component having the activity of hydrolyzing and saccharifying cellulose and/or hemicellulose, or an enzyme component that assists hydrolysis of cellulose and/or hemicellulose.

As the saccharification enzyme, filamentous fungus-derived cellulase is preferably used. Examples of the filamentous fungus-derived cellulase may include cellulases derived from microorganisms such as the genus *Trichoderma*, the genus *Aspergillus*, the genus *Cellulomonas*, the genus *Clostridium*, the genus *Streptomyces*, the genus *Humicola*, the genus *Acremonium*, the genus *Irpex*, the genus *Mucor*, the genus *Talaromyces*, the genus *Phanerochaete*, white rot fungi and brown rot fungi. A cellulase derived from a mutant strain obtained by subjecting the microorganisms to mutation treatment with a mutagen, UV irradiation or the like to improve the productivity of cellulase may also be used. Among such filamentous fungus-derived cellulases, it is preferable to use cellulase derived from the genus *Trichoderma* allowing production of a large amount of enzyme component having a high specific activity in a culture liquid in hydrolysis of cellulose.

The cellulase derived from the genus *Trichoderma* is an enzyme composition containing, as a main component, cellulase derived from a microorganism belonging to the genus *Trichoderma*. The microorganism belonging to the genus *Trichoderma* is not particularly limited but is preferably *Trichoderma reesei*; specific examples thereof may include *Trichoderma reesei* QM9414, *Trichoderma reesei* QM9123, *Trichoderma reesei* RutC-30, *Trichoderma reesei* PC3-7, *Trichoderma reesei* CL-847, *Trichoderma reesei* MCG77, *Trichoderma reesei* MCG80, and *Trichoderma viride* QM9123.

Examples of saccharification enzymes include cellobiohydrolase, endoglucanase, exoglucanase, β-glucosidase, xylanase, xylosidase and the like. One or several kinds of the saccharification enzymes may be used. In addition, hydrolysis of cellulose and hemicellulose can be efficiently performed due to the concerted or complement effect of a plurality of saccharification enzymes, and therefore, an enzyme mixture containing several kinds of the above saccharification enzymes is preferred for use in the hydrolysis of cellulose and hemicellulose.

Cellobiohydrolase is a general term for cellulases that start hydrolysis of cellulose from the terminal portions and release cellobiose, and the group of enzymes belonging to cellobiohydrolase is described as EC number: EC3.2.1.91. Cellulolytic activity can be measured based on the amount of glucose separated when an enzyme is allowed to act on cellulose as a substrate, and a method described in "FILTER PAPER ASSAY FOR SACCHARIFYING CELLULASE" in "Pure & Appl. Chem., Vol. 59, No. 2, pp. 257-268" can be used as a specific method.

Endoglucanase is a general term for cellulases having the activity of hydrolyzing cellulose molecular chains from their central portions, and the groups of enzymes belonging to endoglucanase are described as EC numbers: EC3.2.1.4, EC3.2.1.6, EC3.2.1.39, and EC3.2.1.73. Cellulolytic activity can be measured based on the amount of a reduction sugar separated when an enzyme is allowed to act on carboxymethyl cellulose (CMC) as a substrate, and, for example, a method described in "CARBOXYL CELLULASE ASSAY FOR ENDO-β-1,4-GLUCANASE" in "Pure & Appl. Chem., Vol. 59, No. 2, pp. 257-268" can be used as a specific method.

Exoglucanase is a general term for cellulases allowing hydrolysis from the terminals of cellulose molecular chains, and the groups of enzymes belonging to exoglucanase are described as EC numbers: EC3.2.1.74 and EC3.2.1.58.

β-glucosidase is a general term for cellulases allowing hydrolysis of cellooligosaccharides or cellobiose, and the group of enzymes belonging to β-glucosidase is described as EC number: EC3.2.1.21. Cellobiose decomposition activity (hereinafter also referred to as "BGL activity") can be measured based on the amount of glucose separated when an enzyme is allowed to act on cellobiose as a substrate, and can be measured according to, for example, a method in "Cellobiase assay" described in "Pure & Appl. Chem., Vol. 59, No. 2, pp. 257-268".

Xylanase is a general term for cellulases characterized by acting on hemicellulose or, in particular, xylan, and the group of enzymes belonging to xylanase is described as EC number: EC3.2.1.8.

Xylosidase is a general term for cellulases characterized by acting on xylooligosaccharides, and the group of enzymes belonging to xylosidase is described as EC number: EC3.2.1.37.

Such a saccharification enzyme can be identified by separation using a known technique such as gel filtration, ion exchange, or two-dimensional electrophoresis, amino acid sequence analysis (N-terminal analysis, C-terminal analysis, and mass spectrometry) of the segregated component, and comparison to a database.

Because filamentous fungi produce cellulase in a culture liquid, the culture liquid, as is, may be used as a saccharification enzyme (crude enzyme agent), or a product obtained by purifying and formulating the group of enzymes by a known method may be used as a saccharification enzyme (filamentous fungus-derived cellulase mixture). In the use as the product obtained by purifying and formulating filamentous fungus-derived cellulase, one added with a substance other than the enzyme, such as a protease inhibitor, a dispersant, a dissolution accelerator or a stabilizer may be used as a saccharification enzyme (cellulase formulation).

As the filamentous fungus-derived cellulase, a crude enzyme is preferably used. The crude enzyme is derived from a culture supernatant obtained by culturing a microorganism of the genus *Trichoderma* in an optional period in a culture medium adjusted so that the microorganism produces cellulase. Medium components to be used are not particularly limited, and a culture medium to which cellulose is added for the purpose of promoting the production of cellulase can be commonly used. And, as the crude enzyme, a culture liquid, as is, or a supernatant of the culture obtained only by removing *Trichoderma* cells is preferably used.

The weight ratio of each enzyme component in the crude enzyme is not particularly limited, and, for example, a culture liquid derived from *Trichoderma* reesei contains 50 to 95% by weight of cellobiohydrolase as well as endoglucanase, β-glucosidase and the like as the other components. Because the microorganism of the genus *Trichoderma* produces potent cellulase components in a culture liquid and retains β-glucosidase intracellularly or in cell surfaces, β-glucosidase activity is low in the culture liquid. Thus, β-glucosidase from different species or the same species may be further added to the crude enzyme. As the β-glucosidase from different species, β-glucosidase derived from the genus *Aspergillus* can be preferably used. Examples of the β-glucosidase derived from the genus *Aspergillus* may include Novozyme 188 which is commercially available from Novozymes A/S. A method of adding the β-glucosidase from different species or the same species to the crude enzyme may be a method comprising introducing a gene into the microorganism of the genus *Trichoderma*, culturing the microorganism of the genus *Trichoderma* subjected to gene recombination so as to produce β-glucosidase in a culture liquid, and isolating the culture liquid.

The saccharification treated product obtained in step (2) contains an aqueous sugar solution and a saccharification residual solid. The saccharification residual solid refers to a solid which does not dissolve in water, i.e., a component which scatters light when it is present in water. It refers, for example, to a substance which settles in a super-high-speed centrifugation state of 10000 G, and to a colloidal component substance which does not settle in a super-high-speed centrifugation state but has a supernatant portion forming a colloidal state.

Step (3): Solid-Liquid Separation Step

In step (3), the saccharification treated product obtained in step (2) is separated into an aqueous sugar solution and a saccharification residual solid to remove the saccharification residual solid from the saccharification treated product. In the method of separating the saccharification treated product in step (3), a conventionally known typical separation apparatus can be used. Examples of the separation apparatus include centrifugation-type apparatuses such as screw decanters, disk-type centrifuges, Sharples centrifuges, and vertical centrifuges; pressure-filtration-type apparatuses such as filter presses, pressurization filtration machines, centrifugal filtration machines, screw presses, and belt presses; suction-filtration-type apparatuses such as belt filters, precoat filters, drum-type filtration filters, and vacuum filtration filters and the like. The separation apparatuses may be used singly or in combination of plural kinds. Of these, in particular, the pressure-filtration-type filter press is preferably used from the viewpoint of being excellent in the recovery rate of an aqueous sugar solution, enabling the larger amount of sugar component to be recovered in one solid-liquid separation, and enabling a clear filtrate to be easily obtained.

Filter press is a pressure filtration treatment method using a filter cloth using a woven fabric or a non-woven fabric, and can be easily performed using a commercially available filter cloth and apparatus. The compression pressure in the filter press is not particularly limited but is around 0.01 to 2 MPa, preferably around 0.05 to 1 MPa. The type of the filter press may be vertical or horizontal. As for a liquid sending method, a liquid may be sent with a pump or force-fed with compressed gas. Examples thereof may include "PNEUMA-PRESS" (registered trademark) manufactured by FLSmith; "LASTA FILTER" (registered trademark) manufactured by ISHIGAKI COMPANY, LTD.; "AUTOPAC" (registered trademark) manufactured by Daiki Ataka Engineering Co., Ltd. and the like.

Step (4): Fermentation Step

In step (4), an alcohol fermentation microorganism is cultured with the aqueous sugar solution obtained in step (3) as a fermentation raw material to obtain a culture liquid containing the alcohol fermentation microorganism. Because the aqueous sugar solution obtained in step (3) contains, as a carbon source, a monosaccharide such as glucose or xylose, which can be used by the alcohol fermentation microorganism, the alcohol fermentation microorganism is cultured by using the aqueous sugar solution as the fermentation raw material, to produce alcohol and obtain the culture liquid containing the alcohol fermentation microorganism.

It is essential only that the alcohol fermentation microorganism has the ability to produce alcohol from a sugar. Examples thereof include yeasts such as baker's yeast, bacteria such as *Escherichia coli* and coryneform bacteria, filamentous fungi, actinomycetes and the like, all of which are commonly used in the fermentation industry. The alcohol fermentation microorganism to be used may be ones isolated from the natural environments or may be ones of which the properties are partially modified by mutation or gene recombination. In particular, because an aqueous sugar solution derived from cellulose-containing biomass contains a pentose such as xylose, an alcohol fermentation microorganism having an enhanced metabolic pathway for a pentose can be preferably used.

As a culture medium for alcohol fermentation, there is preferably used a liquid medium containing as appropriate, in addition to the aqueous sugar solution, nitrogen sources, inorganic salts, and, as necessary, organic trace nutrients such as amino acids and vitamins. As the nitrogen source, there are used ammonia gas, aqueous ammonia, ammonium salts, urea, nitrates, and other organic nitrogen sources which are supplementarily used such as oil cakes, soybean-hydrolyzed liquid, casein digests, other amino acids, vitamins, corn steep liquor, yeast or yeast extracts, meat extracts, peptides such as peptone, various fermentation bacterial cells and hydrolysates thereof and the like. As the inorganic salts, phosphates, magnesium salts, calcium salts, iron salts, manganese salts and the like can be added as appropriate.

When the alcohol fermentation microorganism requires a particular nutrient for its growth, the nutrient substance only need to be added as a standard sample or a natural product containing it. Further, an antifoaming agent may be used as necessary.

The culture of the alcohol fermentation microorganism is usually carried out at pH 4 to 8 and a temperature of 20 to 50° C. The pH of a culture liquid is adjusted to a predetermined value which is usually pH 4 to 8 by an inorganic or organic acid, an alkaline substance, as well as urea, calcium carbonate, ammonia gas or the like. In fermentation without the need of oxygen, aeration with nitrogen or carbon dioxide only need to be performed. In fermentation in the need of oxygen, the necessary feeding rate of oxygen can be obtained by using means involving keeping an oxygen concentration at 21% or more by adding oxygen to air, applying pressure to the culture, increasing a stirring speed or increasing a volume of aeration.

The fermentation method may be batch, fed-batch, or continuous fermentation in which a microorganism is recycled. Since it is important that the step of removing the microorganism from the fermentation liquid is performed prior to the distillation step for the fermentation liquid containing the microorganism obtained in the fermentation step, continuous fermentation in which an alcohol fermentation microorganism is recycled through a microfiltration membrane is preferred, and examples thereof include a method described in WO 2007/97260 and the like.

Step (5): Microorganism Removing Step

In step (5), the alcohol fermentation microorganism is removed from the culture liquid containing the alcohol fermentation microorganism obtained in step (4), to obtain an aqueous solution containing alcohol (alcohol fermentation liquid). It is essential only that the removal of the alcohol fermentation microorganism from the culture liquid is a method enabling separation into an alcohol fermentation microorganism and an alcohol fermentation liquid. Examples of the method of removing the alcohol fermentation microorganism from the culture liquid include a method of centrifugation with by a disk-type centrifuge, a Sharples centrifuge, a vertical centrifuge or the like; a method of separation into a culture liquid and an alcohol fermentation microorganism through a microfiltration membrane; a method of performing continuous fermentation in combination of such a fermentation method as in step (4) and the separation method or the like. Of these, the method of separation into a culture liquid and an alcohol microorganism through a microfiltration membrane is preferably applied.

When the method of separation into a culture liquid and an alcohol microorganism through a microfiltration membrane is used, the type of the microfiltration membrane is not particularly limited as long as it is the type of filtration by sweeping flow on a membrane surface, and any of a flat membrane, a hollow fiber membrane, a tube membrane and the like may be employed. Examples of the material of the membrane include inorganic membranes of ceramics such as alumina, titania, and zirconia, glass, metals and the like; or organic membranes of cellulose acetate-based, nitrocellulose-based, aliphatic polyamide-based, polysulfone-based, polyolefin-based, polyacrylonitrile-based, polyether sulfone-based, polyvinyl chloride-based, polyvinyl alcohol-based, and fluorine-based polymers and the like.

The conditions of the filtration of the culture liquid through the microfiltration membrane will be described. A sweeping flow effect on a membrane surface is increased with increasing a membrane surface speed for sweeping flow on a separation membrane surface. However, when the speed is a certain speed or more, the pressure loss becomes great, compaction of a gel layer in the vicinity of the membrane occurs, and a membrane permeation flux and recovery rate of an alcohol fermentation liquid in a culture liquid decrease. When the membrane surface speed is too low, the effect of peeling the gel layer is deteriorated to decrease the recovery rate of the alcohol fermentation liquid in the culture liquid although the pressure loss is decreased to avoid compaction. Thus, it is appropriate that the membrane surface speed is substantially 0.5 to 3 m/s.

A transmembrane pressure difference in the filtration of a culture liquid through a microfiltration membrane refers to an average transmembrane pressure difference between an inlet and an outlet, and is usually preferably 2.0 kgf/cm$^2$ or less, and more preferably 0.2 to 1.5 kgf/cm$^2$. When the transmembrane pressure difference is 0.2 kgf/cm$^2$ or more, reduction in permeation flux can be suppressed to suppress the deterioration of treatability. When the transmembrane pressure difference is 2.0 kgf/cm$^2$ or less, the occurrence of clogging of the membrane due to, e.g., the compaction of the gel layer on the membrane surface can be suppressed to suppress reduction in permeation flux. A method of applying a transmembrane pressure difference may be a stock solution side pressurization type, a permeate side decompression type, or a combination thereof.

An operation temperature in the filtration of the culture liquid through the microfiltration membrane is usually 0 to 40° C. and preferably 5 to 30° C. When the operation temperature is 0° C. or more, the increased viscosity of the culture liquid can be suppressed, and therefore, the occurrence of reduction in membrane permeation flux can be suppressed. When the operation temperature is 40° C. or less, the deterioration of the properties of the culture liquid can be suppressed.

Step (6): Distillation Step

In step (6), the alcohol fermentation liquid obtained in step (5) is distilled and separated into purified alcohol and distillation residual liquid to recover the purified alcohol. For the distillation of the alcohol in step (6), a conventionally known distillation method can be used.

For example, when the alcohol is ethanol, ethanol forms water and an azeotropic mixture (for example, the composition of azeotropic ethanol includes 95.6% by weight of ethanol and about 4.4% by weight of water at normal pressure) and therefore, it is impossible to obtain an anhydride in usual distillation. Thus, when dehydrated ethanol is obtained from azeotropic ethanol by distillation, a method of performing azeotropic distillation using an azeotropic solvent such as pentane or cyclohexane, or a method of performing extractive distillation using an extraction solvent such as ethylene glycol is commonly performed. In the azeotropic mixture forming two components of ethanol and water, gas-liquid equilibrium can be changed by the effect of the extraction solvent to distill only ethanol in the extractive distillation method.

Step (7): Reverse Osmosis Membrane Step

In step (7), the distillation residual liquid obtained in step (6) is filtered to be separated into a permeate and a retentate and to recover the retentate. The distillation residual liquid is preferably filtered using a reverse osmosis membrane. The saccharification residual solid in the saccharification treated product is removed in advance in step (3) before the aqueous sugar solution is fermented in step (4), and the alcohol fermentation liquid from which the alcohol fermentation microorganism in the culture liquid has been removed is formed in advance in step (5) before the alcohol is distilled in step (6). Thus, the alcohol fermentation liquid is distilled in the state of reducing impurities such as solid substances and suspended substances. Thus, the distillation residual liquid obtained in step (6) contains far less impurities than a distillation residual liquid obtained in a conventional process, and the COD of the distillation residual liquid is a low value. It is known that COD concentration at which biological treatment is possible has an upper limit. In step (7), the compression rate of the distillation residual liquid obtained by passing and filtering the distillation residual liquid obtained in step (6) through the reverse osmosis membrane can be allowed to be higher than that of a distillation residual liquid obtained in a conventional process. As a result, the amount of retentate subjected to discharge treatment is greatly reduced in step (8) mentioned later.

The reverse osmosis membrane (RO membrane) is generally defined as a "membrane having a function of blocking salts including monovalent ions". The membrane is thought to have microscopic openings ranging from about several angstroms to several nanometers and mainly used to remove ion components, for example, in desalination of sea water or production of ultrapure water.

Examples of materials of the reverse osmosis membrane include composite membranes with cellulose acetate-based polymer as a functional layer (hereinafter also referred to as cellulose acetate-based reverse osmosis membranes) and composite membranes with polyamide as a functional layer (hereinafter also referred to as polyamide-based reverse osmosis membranes). Examples of the cellulose acetate-based polymer include ones that utilize solely organic acid esters of cellulose such as cellulose acetate, cellulose diacetate, cellulose triacetate, cellulose propionate, or cellulose butyrate or a mixture thereof; and a mixed ester. Examples of polyamides include a linear polymer or a cross-linked polymer with aliphatic and/or aromatic diamines as a monomer.

A polyamide-based reverse osmosis membrane is preferably used. This is because when a cellulose acetate-based reverse osmosis membrane is used over an extended time period, a saccharification enzyme used in a previous step, in particular, a part of cellulase components may permeate to decompose cellulose which is a membrane material.

As for the form of the membrane, ones in an appropriate form such as a flat membrane type, a spiral type, or a hollow fiber type can be used.

Examples of the reverse osmosis membrane include, in addition to ultra low pressure types SUL-G10 and SUL-G20, and low pressure types SU-710, SU-720, SU-720F, SU-710L, SU-720L, SU-720LF, SU-720R, SU-710P, and SU-720P, which are polyamide-based reverse osmosis membrane modules manufactured by Toray Industries, Inc.; high pressure types SU-810, SU-820, SU-820L, and SU-820FA containing UTC80 as a reverse osmosis membrane; acetic acid cellulose-based reverse osmosis membranes SC-L100R, SC-L200R, SC-1100, SC-1200, SC-2100, SC-2200, SC-3100, SC-3200, SC-8100, and SC-8200, which are manufactured by the same company; NTR-759HR, NTR-729HF, NTR-70SWC, ES10-D, ES20-D, ES20-U, ES15-D, ES15-U, and LF10-D, which are manufactured by Nitto Denko Corporation Co., Ltd.; RO98pHt, RO99, HR98PP, and CE4040C-30D, which are manufactured by Alfa Laval; GE Sepa manufactured by GE; BW30-4040, TW30-4040, XLE-4040, LP-4040, LE-4040, SW30-4040, and SW30HRLE-4040, which are manufactured by Filmtec; TFCHR and TFC-ULP, which are manufactured by KOCH; ACM-1, ACM-2, and ACM-4, which are manufactured by TRISEP and the like.

In the filtration through the reverse osmosis membrane, pressure may be applied, and the filtration pressure is preferably 0.1 to 8 MPa. A filtration pressure of 0.1 MPa or more enables decrease in membrane permeation speed to be suppressed while a filtration pressure of 8 MPa or less enables the damages of the membrane to be suppressed. Further, a filtration pressure of 0.5 to 7 MPa is more preferred because of resulting in a high membrane permeation flux, enabling a distillation residual liquid to be efficiently permeated, and being less likely to cause the damages of the membrane, and a filtration pressure of 1 to 6 MPa is still more preferred.

"Passing and filtering distillation residual liquid through reverse osmosis membrane" refers to passing and filtering a distillation residual liquid through a reverse osmosis membrane without performing treatment of reducing in advance COD in the distillation residual liquid. In other words, "passing and filtering distillation residual liquid through reverse osmosis membrane" includes directly passing and filtering a distillation residual liquid through a reverse osmosis membrane, as well as "passing and filtering distillation residual liquid through reverse osmosis membrane" is intended to also include filtration of a distillation residual liquid after solid-liquid separation treatment when the distillation residual liquid is subjected in advance to the solid-liquid separation treatment to remove solid contents and is passed and filtered through a reverse osmosis membrane, and COD is not changed before and after the solid-liquid separation treatment. Preferred examples of "passing and filtering distillation residual liquid through reverse osmosis membrane" include directly passing and filtering a distillation residual liquid through a reverse osmosis membrane.

The retentate obtained by passing and filtering the distillation residual liquid through the reverse osmosis membrane is supplied to step (8), while the permeate permeating through the reverse osmosis membrane can be reused as process water and can be used, for example, as water and vapor in step (1), or as water in step (2) or step (4).

Step (8): Discharge Treatment Step

In step (8), discharge treatment is performed to discharge the retentate from the reverse osmosis membrane obtained in step (7) to the outside of a process. Examples of methods for the discharge treatment of the retentate include an anaerobic treatment step or an aerobic treatment step in which biological treatment is performed. An anaerobic treatment step and an aerobic treatment step are used.

The biological treatment is the step of decomposing BOD or COD with microorganisms, examples of the anaerobic treatment step include methane fermentation methods and the like, and examples of the aerobic treatment step include activated sludge methods and the like.

The retentate is subjected to the discharge treatment and then discharged as discharge water to the outside of the process.

As described above, according to the method of producing alcohol, the saccharification residual solid in the saccharification treated product is removed in advance in step (3) before the aqueous sugar solution is fermented in step (4), and the alcohol fermentation microorganism in the culture liquid is removed in advance in step (5) before the alcohol fermentation liquid is distilled in step (6), whereby the alcohol fermentation liquid with a small amount of impurities can be distilled. Thus, the amount of impurities in the distillation residual liquid remaining after recovering alcohol from the alcohol fermentation liquid can be greatly reduced. As a result, the distillation residual liquid can be passed through the reverse osmosis membrane, compression of the distillation residue liquid in step (7) and the great reduction in the amount of the retentate treated in step (8) are enabled. Therefore, the load of the discharge treatment can be greatly reduced.

Further, according to the method of producing alcohol, the distillation residual liquid obtained in step (6) contains far less impurities than a distillation residual liquid obtained in a conventional process, the COD of the distillation residual liquid is a low value, and therefore, a compression rate for the reverse osmosis membrane can be enhanced. The amount of the retentate subjected to the discharge treatment in step (8) can be greatly reduced.

EXAMPLES

The method of producing alcohol will be described below with reference to examples to particularly describe a method of producing ethanol in more detail. In reference examples, manipulations common to Examples and Comparative Examples will be described. This disclosure is not, however, limited to these examples.

In the reference examples, the manipulations are common to Examples and Comparative Examples. Further, FIG. 2 to FIG. 6 are drawings showing flows of the steps of producing ethanol from cellulose-containing biomass of the Examples or Comparative Examples.

Reference Example 1 Method of Analyzing Ethanol

In the gas chromatography (GC) conditions shown below, the concentration of ethanol was detected by a detector, calculated, and quantified by comparing with a standard sample.

Gas chromatography apparatus: Shimadzu GC-2010 (manufactured by SHIMADZU CORPORATION)

Capillary column: TC-1 (inner diameter of 0.53 mm, length of 15 m, film thickness of 1.50 μm) (manufactured by GL Sciences Inc.)

Detector: flame ionization detector (FID)

Reference Example 2 Method of Measuring COD

Measurement of COD was performed in the following procedure:
1. With a whole pipette, 100 ml of sample was accurately measured.
2. Added were 10 ml of 5% sulfuric acid and 10 ml of 0.02/5 M aqueous potassium permanganate solution measured with a whole pipette, to heat the resultant for 10 minutes.
3. Added was 10 ml of 0.01 M oxalic acid measured with a whole pipette.
4. The resultant was titrated with a 0.02/5 M aqueous potassium permanganate solution.

Reference Example 3 Step of Pretreatment of Cellulose-Containing Biomass (Hydrothermal Treatment)

Hydrothermal treatment was used as a method of pretreating cellulose-containing biomass. As the cellulose-containing biomass, 1 kg of rice straw was used. Into water, 2 kg of the cellulose-containing biomass was dipped, and subjected to autoclave-treatment (manufactured by Nitto Koatsu Co., Ltd.) at 180° C. for 20 minutes while being stirred, to obtain a pretreated product. The pressure was 10 MPa.

Reference Example 4 Saccharification Step

Water was added to the pretreated product obtained in Reference Example 3 to have a concentration of 15% by weight, thereafter, cellulase derived from *Trichoderma* sp. (the genus *Trichoderma*) (Sigma-Aldrich Co. LLC.) as cellulase and Novozyme 188 (β-glucosidase formulation derived from *Aspergillus niger*, Sigma-Aldrich Co. LLC.) were further added, and glycation reaction was caused while stirring and mixing the resultant at 50° C. for 1.5 days, to obtain a saccharification treated product containing an aqueous sugar solution and saccharification residual solids.

Reference Example 5 Filter Press Step

To 1 kg of the saccharification treated product obtained in Reference Example 4 (in FIG. 5) or 1 kg of the residual liquid after the distillation step of Reference Example 7 (in FIG. 2), 500 g of filtration treatment auxiliary was added to make 1.5 kg in total, and the resultant was stirred to make a homogeneous slurry liquid, which was then subjected to filter press (using a small filter device MO-4 manufactured by YABUTA Industries Co., Ltd.). Because of the high suspended characteristics of a filtrate in an early stage, the filtrate obtained during 1 minute after the start of the filtration was returned to a raw water tank. As a filter cloth, T2731C was used. A filtrate obtained after a lapse of 1 minute following the start of the filtration was recovered to obtain 0.5 kg of aqueous sugar solution (in FIG. 5) or 0.5 kg of distillation residual liquid (in FIG. 2).

Reference Example 6 Fermentation Step

Wine yeast (*Saccharomyces cerevisiae* OC2 strain) was used as ethanol fermentation yeast. As a fermentation culture medium, a product obtained by adding cellulase as shown in Reference Example 4 to 1 kg of the pretreated solid contents obtained after the pretreatment step (in FIG. 2), or a liquid obtained by adding 5 g of yeast extract and 5 g of ammonium sulfate to 0.5 kg of aqueous sugar solution (in FIG. 5) was used. For a seed culture liquid into which inoculation was performed in the fermentation step, 50 g/L of glucose, 5 g/L of yeast extract, and 5 g/L of ammonium sulfate were used to culture at 30° C. for 1 day. A seed culture liquid intake amount was set at 10% of the fermentation culture medium. The fermentation step was carried out for 1.5 days by maintaining temperature at 30° C. without aeration/stirring. Such a liquid obtained after a fermentation step is referred to as a culture liquid (containing ethanol fermentation yeast).

Reference Example 7 Distillation Step

A culture liquid or an ethanol fermentation liquid obtained by removing ethanol fermentation yeast from the culture liquid was put into a distillation apparatus and was heated to 120° C. to recover a 37% ethanol solution from a tower top. On the other hand, the COD and volume of the distillation residual liquid were measured.

Reference Example 8 Reverse Osmosis Membrane Step

A cross-linked wholly aromatic polyamide-based reverse osmosis membrane UTC80 (manufactured by Toray Industries, Inc.) was used as a reverse osmosis membrane, the temperature of raw water to be supplied was adjusted to 25° C., and the pressure of a high pressure pump 3 was adjusted to 3 MPa, to remove the permeate. The compression rate was calculated by volume in retentate side/volume of raw water to be supplied×100(%). Further, the upper limit of the compression of discharged liquid in the reverse osmosis membrane step was set at a level where the COD of a concentrated liquid was 100 g/L.

Reference Example 9 Microfiltration Step

A dead-end filtration operation through a microfiltration membrane ("Stericup HV" 0.45 μm (registered trademark) manufactured by Millipore Corporation) was carried out using 100 ml of treatment liquid (distillation residual liquid (in FIG. 4) or culture liquid (in FIG. 5) after filter press). It was a constant pressure filtration operation at a suction pressure of 80 kPa. From a membrane permeation side, 90 ml of distillation residual liquid (in FIG. 4) or 90 ml of ethanol fermentation liquid (in FIG. 5) subjected to the microfiltration step was recovered.

Comparative Example 1: Evaluation of Load in Discharge Treatment Step in Process Shown in FIG. 2

Figure 2:
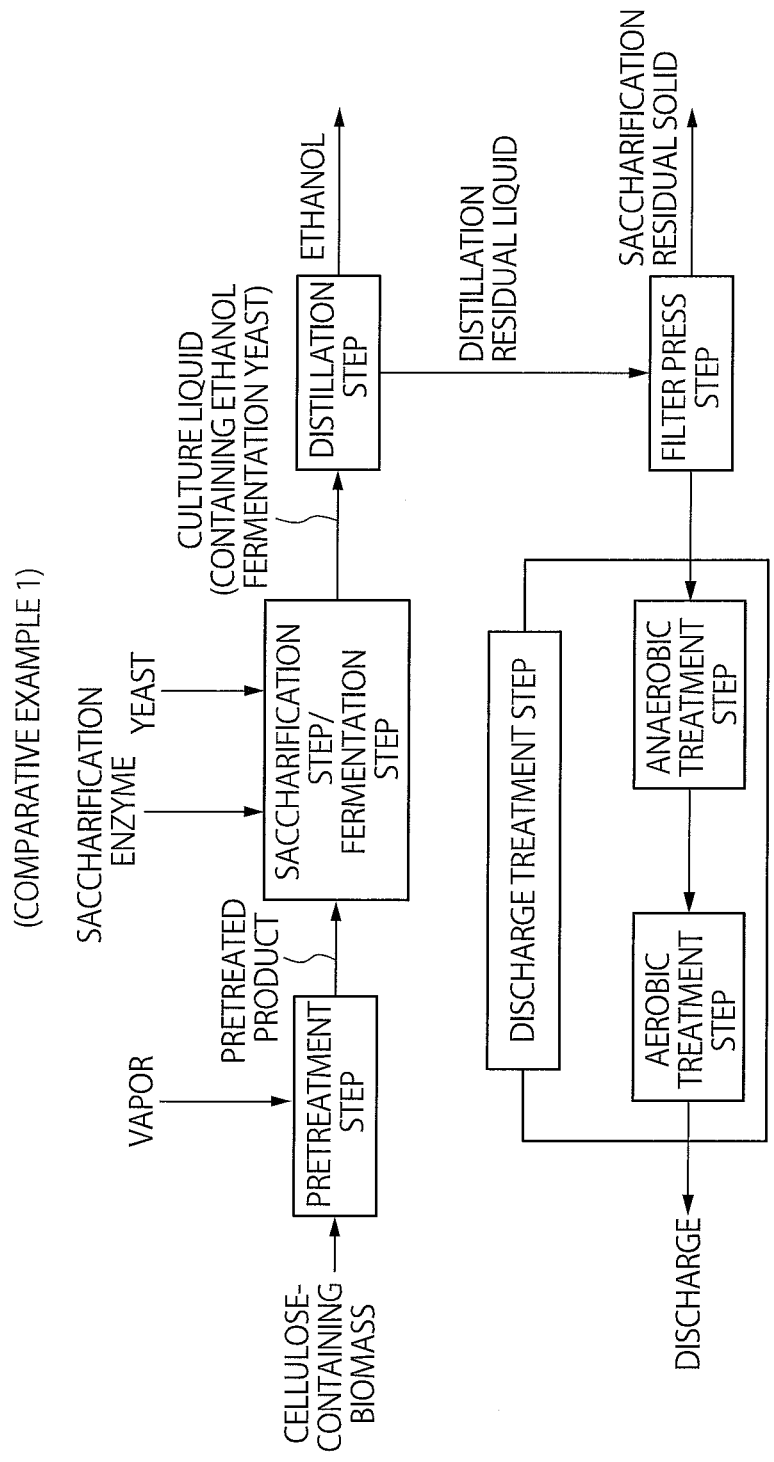
FIG. 2 is a drawing showing a flow of the steps of producing ethanol from cellulose-containing biomass of Comparative Example 1.

FIG. 2 is a drawing showing a method of producing ethanol of this comparative example, which is one aspect of a conventional method of producing ethanol. According to the above reference examples, 1 kg of cellulose-containing biomass was subjected to treatment in the pretreatment step, the saccharification step, and the fermentation step in this order, and the obtained culture liquid was subjected to the distillation step to purify ethanol. The distillation residual liquid in the process shown in FIG. 2 was 5.8 L. Further, COD was 89 g/L. The distillation residual liquid was not able to be passed through a reverse osmosis membrane because of containing ethanol fermentation yeast and saccharification residue solids. The distillation residual liquid obtained in FIG. 2 was subjected to filter press to acquire 4.8 L of liquid from which the saccharification residual solids were removed. In the discharge treatment step, the COD of this liquid was reduced, and the liquid was discharged.

Comparative Example 2: Evaluation of Application of Reverse Osmosis Membrane Step in Process Shown in FIG. 3

Figure 3:
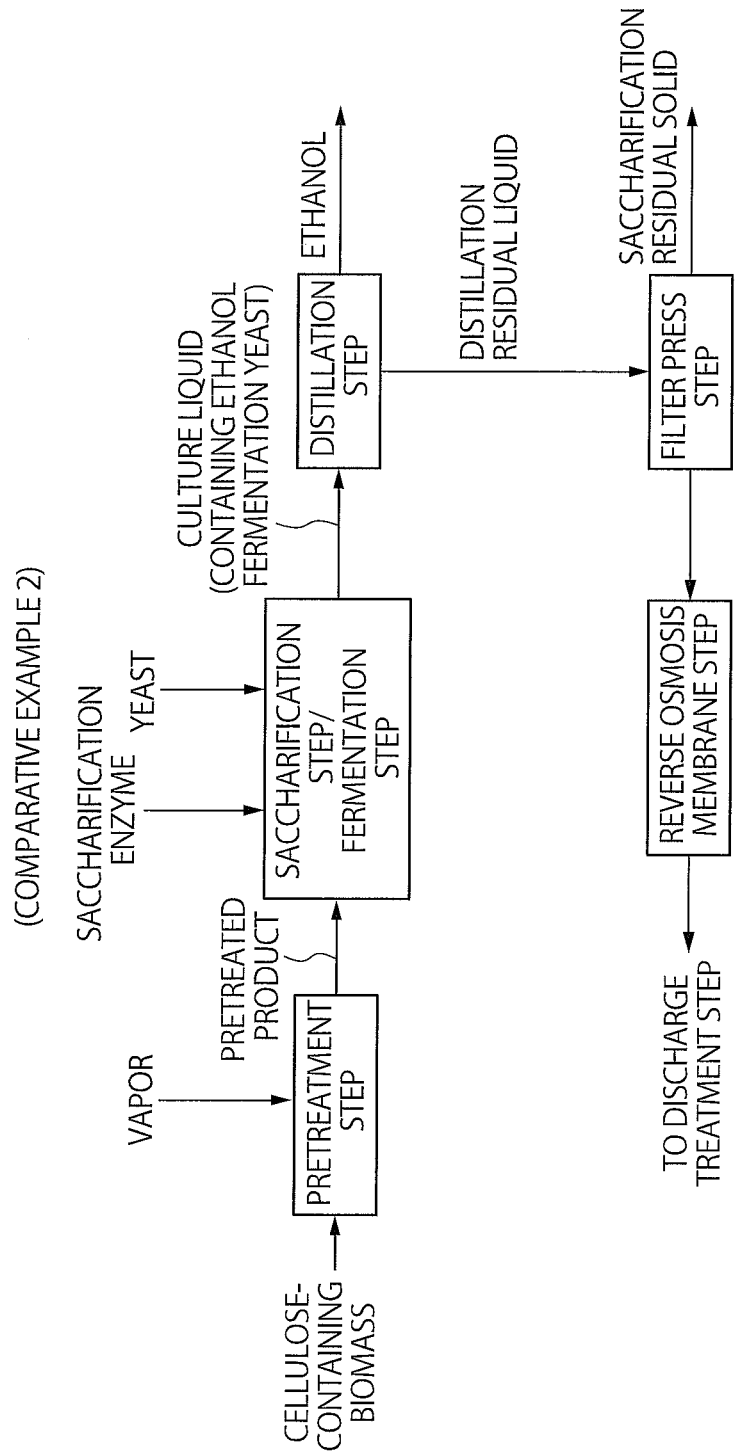
FIG. 3 is a drawing showing a flow of the steps of producing ethanol from cellulose-containing biomass of Comparative Example 2.

FIG. 3 is a drawing showing a method of producing ethanol of this comparative example. In this comparative example, the reverse osmosis membrane step was applied after the filter press step in the process of FIG. 2. A distillation residual liquid obtained in FIG. 2 was subjected to filter press to acquire 4.8 L of liquid from which saccharification residual solids were removed. The liquid subjected to the filter press was filtered through a reverse osmosis membrane by the manipulation shown in Reference Example 7, a permeation rate (rate at which a permeate came out) was sharply decreased, and clogging of the reverse osmosis membrane finally prevented 100 ml or more of permeate from being acquired. Accordingly, the compression rate in the reverse osmosis membrane step was 97.9%, and compression hardly occurred. Reduction in the amount of discharged liquid supplied to the discharge treatment step was able to be hardly achieved by adding the reverse osmosis membrane step.

Comparative Example 3: Evaluation of Application of Reverse Osmosis Membrane Step in Process Shown in FIG. 4

Figure 4:
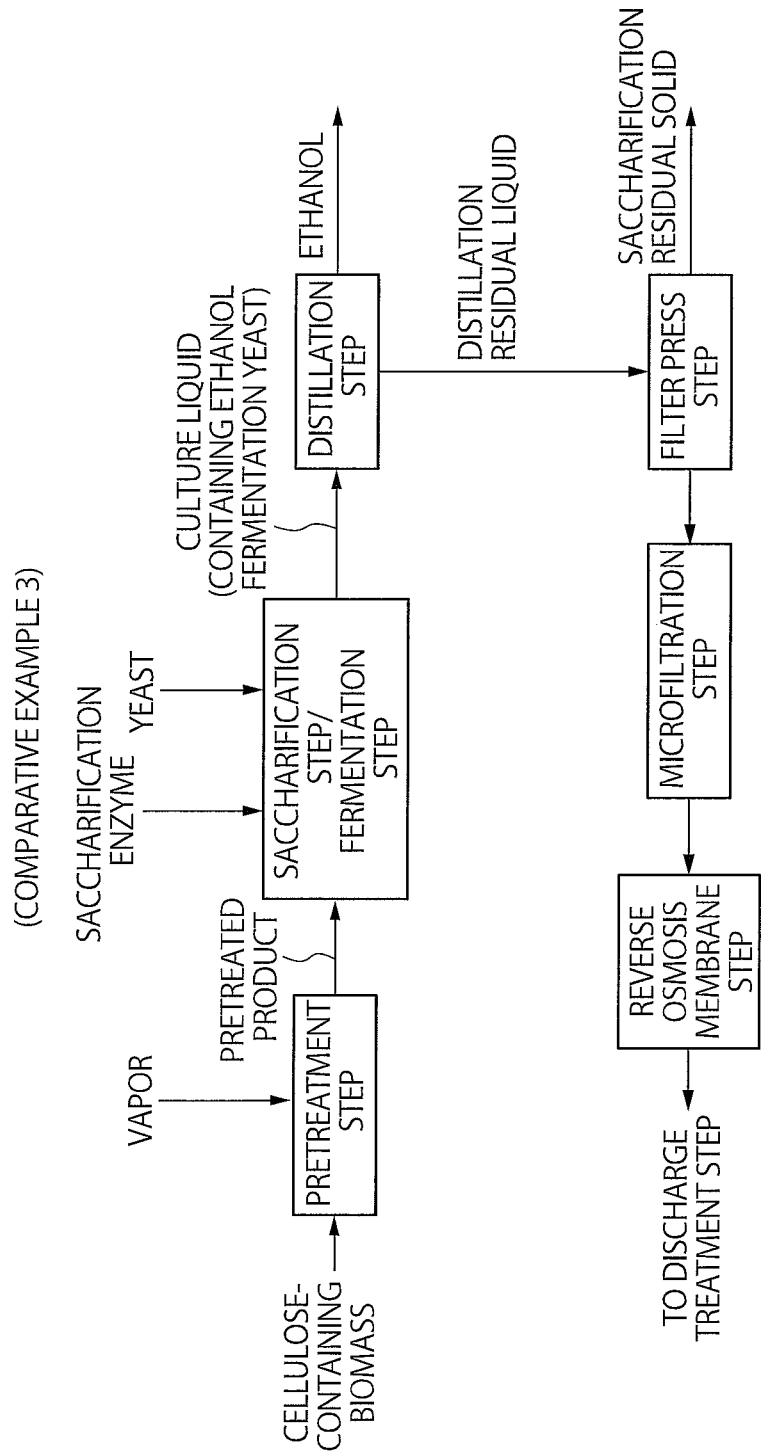
FIG. 4 is a drawing showing a flow of the steps of producing ethanol from cellulose-containing biomass of Comparative Example 3.

FIG. 4 is a drawing showing a method of producing ethanol of this comparative example. In this comparative example, the microfiltration step and the reverse osmosis membrane step were applied after the filter press step in the process of FIG. 2. The distillation residual liquid obtained in FIG. 2 was subjected to filter press, and the liquid was then passed through a microfiltration membrane to acquire 4.7 L of liquid from which fine solids were further removed. When the obtained liquid was filtered through a reverse osmosis membrane by the manipulation shown in Reference Example 7, the amount of a permeate was improved compared to Comparative Example 2, but COD reached 100 g/L at the time of acquiring 0.4 L of permeate after a lapse of 15 hours. It was impossible to supply it to the discharge treatment step at COD concentration that was not less than it. Accordingly, the limit of the compression rate in the reverse osmosis membrane step was 91.4%, and compression hardly occurred.

Example 1: Evaluation of Load in Discharge Treatment Step in Process Shown in FIG. 5

Figure 5:
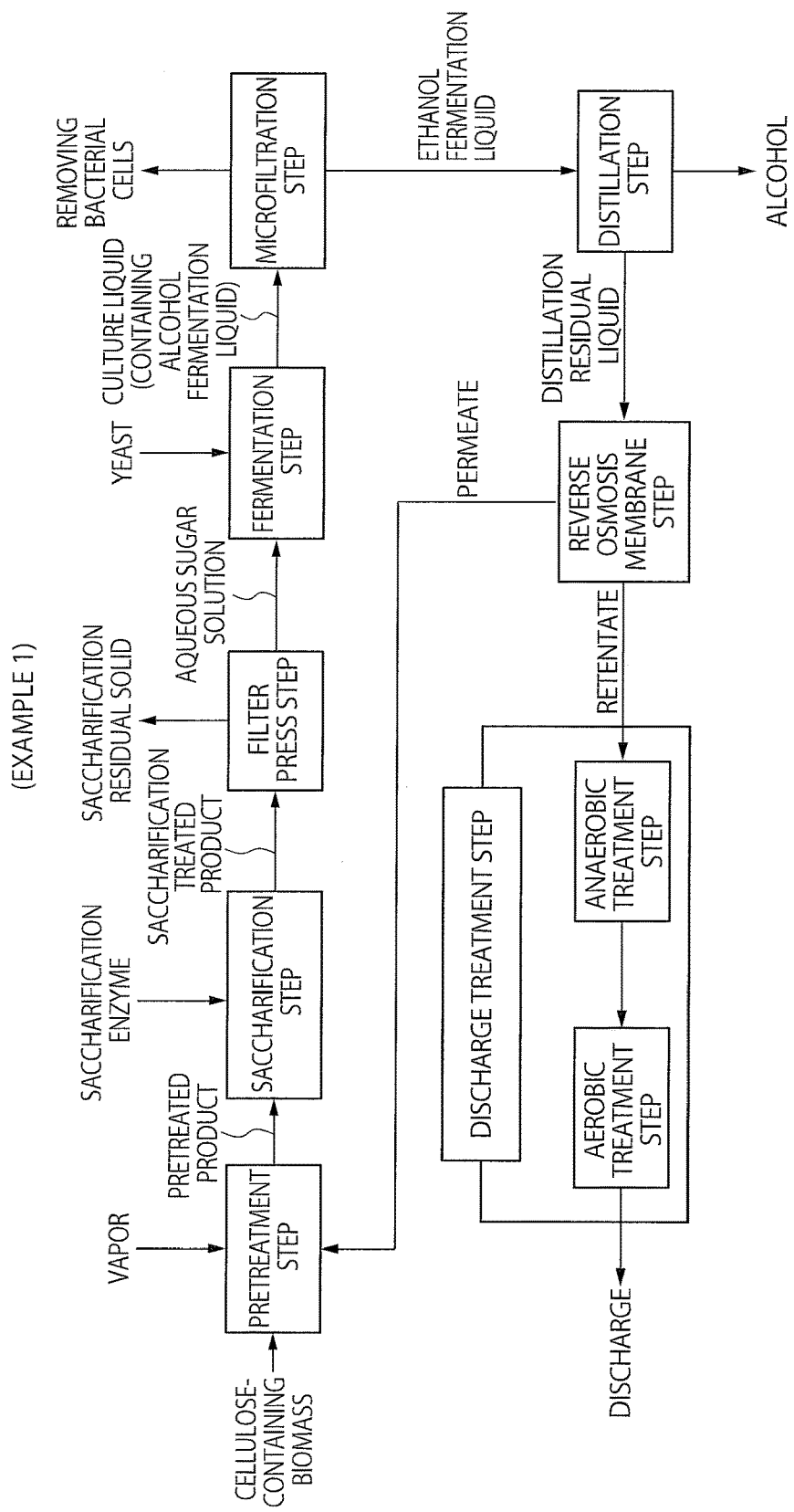
FIG. 5 is a drawing showing a flow of the steps of producing ethanol from cellulose-containing biomass of Example 1.

FIG. 5 is a drawing showing a method of producing ethanol of this example. According to the above reference examples, 1 kg of cellulose-containing biomass was subjected to treatment in the pretreatment step, the saccharification step, the filter press section, the fermentation step, and the microfiltration step in this order, and the obtained ethanol fermentation liquid was subjected to the distillation step to purify ethanol. As a result, the distillation residual liquid in the process shown in FIG. 5 was 4.7 L and has a COD of 20 g/L, which greatly decreased compared to each comparative example described above. When the distillation residual liquid was passed through a reverse osmosis membrane, a permeation rate is obviously higher than that in Comparative Example 3, and 2.4 L of permeate was able to be acquired just for 2 hours. Further, the COD of a retentate in the reverse osmosis membrane step was 38 g/L. As a result of further passing and concentrating the retentate through the reverse osmosis membrane for 2 hours, 1.2 L of retentate was able to be acquired, and its COD was 75 g/L. Thus, the compression rate in the reverse osmosis membrane step was finally 25.5%, and the volume of the retentate from the reverse osmosis membrane, to be subjected to the discharge treatment, was able to be significantly compressed.

As is clear from the results, in Example 1 (FIG. 5), the distillation residual liquid was able to be more efficiently compressed and the COD of the distillation residual liquid was able to be greatly reduced in the reverse osmosis membrane step although the kinds and number of the steps were the same as those in Comparative Example 3 (FIG. 4) as for the process prior to the discharge treatment step. Further, the liquid volume of the retentate to be subjected to the discharge treatment step in Example 1 was able to be reduced to about ¼ of that in Comparative Example 1 (FIG. 2).

Figure 6:
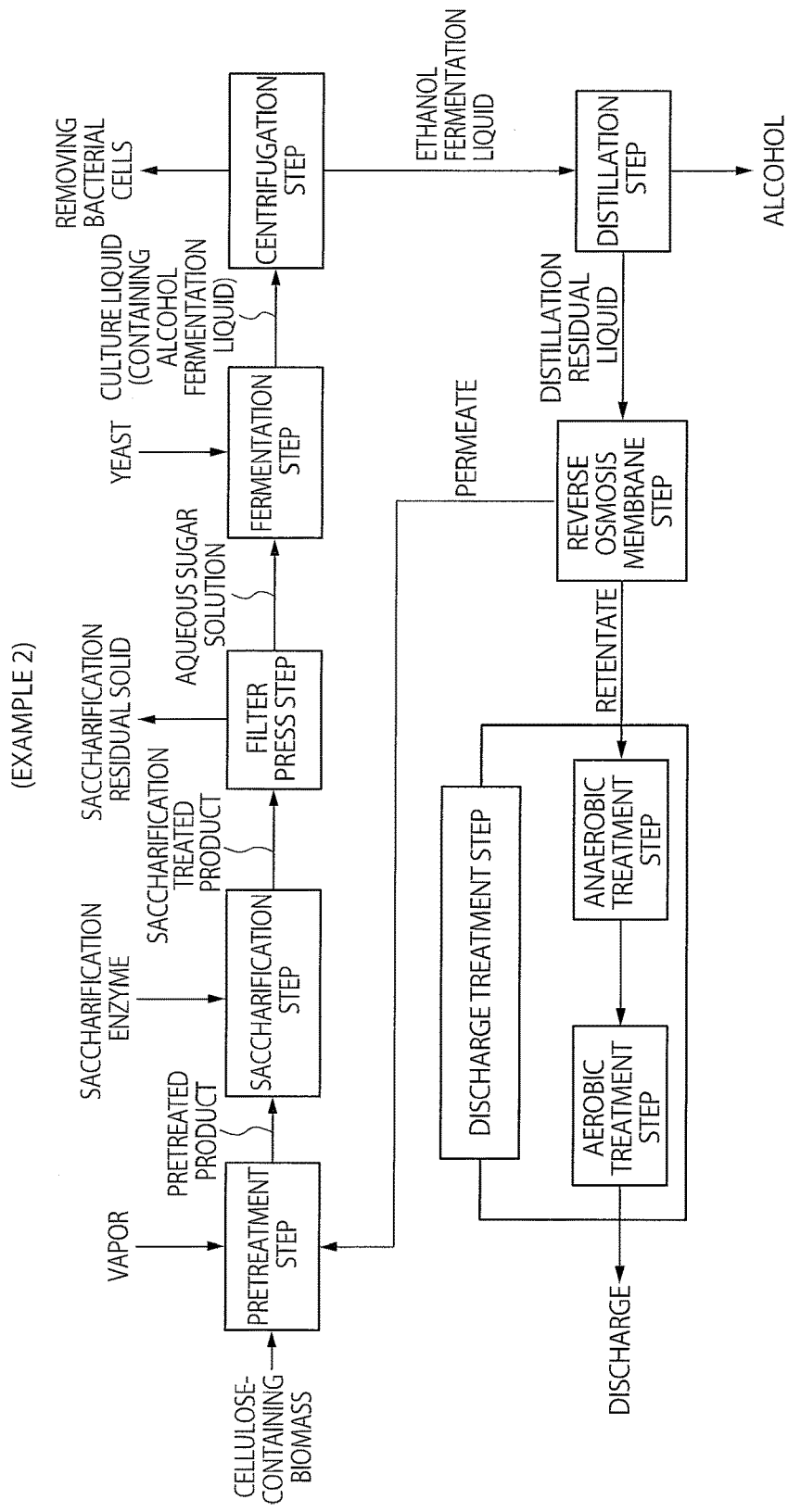
FIG. 6 is a drawing showing a flow of the steps of producing ethanol from cellulose-containing biomass of Example 2.

Example 2: Evaluation of Load in Discharge Treatment Step in Case of Carrying Out Centrifugation Step Instead of Microfiltration Step FIG. 6 is a drawing showing a method of producing ethanol of this example. A culture liquid was obtained by a method similar to that in Example 1, and the obtained culture liquid was then centrifuged at 150 G to remove yeast in the culture liquid, and was distilled. A distillation residual liquid was 4.5 L, and its COD was 25 g/L. Then, when the distillation residual liquid was passed through a reverse osmosis membrane, 2.4 L of permeate was able to be acquired just for 3 hours. Further, the COD of a retentate obtained by passing the distillation residual liquid through a reverse osmosis membrane was 50 g/L. As a result of further passing and concentrating the retentate through the reverse osmosis membrane for 3 hours, 1.5 L of retentate was able to be acquired, and its COD was 80 g/L. Thus, the compression rate in the reverse osmosis membrane step was finally 33.3%, and the volume of the retentate from the reverse osmosis membrane, to be subjected to the discharge treatment, was able to be significantly compressed.

As is clear from the results, like Example 1 described above, in Example 2, the distillation residual liquid was able to be more efficiently compressed and the COD of the distillation residual liquid was able to be greatly reduced in the reverse osmosis membrane step although the kinds and number of the steps were the same as those in Comparative Example 3 (FIG. 4). Further, the volume of the liquid to be subjected to the discharge treatment step in Example 2 was able to be reduced to about ⅓ of that in Comparative Example 1 (FIG. 2).

The invention claimed is:
1. A method of producing alcohol from cellulose-containing biomass comprising steps (1) to (8):
step (1): pretreating a cellulose-containing biomass;
step (2): saccharifying the pretreated cellulose-containing biomass obtained in step (1) with a saccharification enzyme;
step (3): removing a saccharification residual solid from a saccharification treated product obtained in step (2);
step (4): culturing an alcohol fermentation microorganism with an aqueous sugar solution obtained in step (3) as a fermentation raw material;

step (5): removing the alcohol fermentation microorganism from a culture liquid containing the alcohol fermentation microorganism obtained in step (4);

step (6): distilling the alcohol fermentation liquid obtained in step (5) to recover alcohol;

step (7): passing and filtering a distillation residual liquid obtained in step (6) through a reverse osmosis membrane; and step (8): performing biological treatment of discharging a retentate obtained in step (7), wherein removing the saccharification residual solid in step (3) and removing the alcohol fermentation microorganism in step (5) are associated with a reduction of the amount of the retentate obtained in step (7).

2. The method according to claim 1, wherein step (5) passes and filters the culture liquid containing the alcohol fermentation microorganism obtained in step (4) through a microfiltration membrane.

3. The method according to claim 2, wherein step (3) uses a filter press.

4. The method according to claim 2, wherein a permeate obtained through the reverse osmosis membrane in step (7) is reused as process water for step (1), (2), or (4).

5. The method according to claim 2, wherein step (7) directly passes and filters the distillation residual liquid obtained in step (6) through the reverse osmosis membrane.

6. The method according to claim 2, wherein the alcohol is methanol, ethanol, propanol or butanol.

7. The method according to claim 1, wherein step (3) uses a filter press.

8. The method according to claim 7, wherein a permeate obtained through the reverse osmosis membrane in step (7) is reused as process water for step (1), (2), or (4).

9. The method according to claim 7, wherein step (7) directly passes and filters the distillation residual liquid obtained in step (6) through the reverse osmosis membrane.

10. The method according to claim 7, wherein the alcohol is methanol, ethanol, propanol or butanol.

11. The method according to claim 1, wherein a permeate obtained through the reverse osmosis membrane in step (7) is reused as process water for step (1), (2), or (4).

12. The method according to claim 11, wherein step (7) directly passes and filters the distillation residual liquid obtained in step (6) through the reverse osmosis membrane.

13. The method according to claim 11, wherein the alcohol is methanol, ethanol, propanol or butanol.

14. The method according to claim 1, wherein step (7) directly passes and filters the distillation residual liquid obtained in step (6) through the reverse osmosis membrane.

15. The method according to claim 14, wherein the alcohol is methanol, ethanol, propanol or butanol.

16. The method according to claim 1, wherein the alcohol is methanol, ethanol, propanol or butanol.

17. The method according to claim 1, wherein the step (7) has a compression rate defined as volume of the retentate/volume of the distillation residual liquid×100(%) is 33.3% or less.

18. The method according to claim 1, wherein removing the saccharification residual solid in step (3) and removing the alcohol fermentation microorganism in step (5) are associated with the distillation residual liquid in step (7) having a reduction in chemical oxygen demand (COD) level.

19. The method according to claim 1, wherein the distillation residual liquid of step (7) has a COD level of 25 g/L or less.

20. A method of producing alcohol from cellulose-containing biomass, comprising steps (1) to (8):

step (1): pretreating a cellulose-containing biomass;

step (2): saccharifying the pretreated cellulose-containing biomass obtained in step (1) with a saccharification enzyme;

step (3): removing a saccharification residual solid from a saccharification treated product obtained in step (2);

step (4): culturing an alcohol fermentation microorganism with an aqueous sugar solution obtained in step (3) as a fermentation raw material;

step (5): removing the alcohol fermentation microorganism from a culture liquid containing the alcohol fermentation microorganism obtained in step (4) by centrifugation or microfiltration separation;

step (6): distilling the alcohol fermentation liquid obtained in step (5) to recover alcohol;

step (7): passing and filtering a distillation residual liquid obtained in step (6) through a reverse osmosis membrane; and step (8): performing biological treatment of discharging a retentate obtained in step (7).

21. A method of producing alcohol from cellulose-containing biomass, the method comprising steps (1) to (8):

step (1): pretreating a cellulose-containing biomass;

step (2): saccharifying the pretreated cellulose-containing biomass obtained in step (1) with a saccharification enzyme;

step (3): removing a saccharification residual solid from a saccharification treated product obtained in step (2) with a filter press;

step (4): culturing an alcohol fermentation microorganism with an aqueous sugar solution obtained in step (3) as a fermentation raw material;

step (5): removing the alcohol fermentation microorganism from a culture liquid containing the alcohol fermentation microorganism obtained in step (4) by centrifugation or microfiltration separation;

step (6): distilling the alcohol fermentation liquid obtained in step (5) to recover alcohol;

step (7): passing and filtering a distillation residual liquid obtained in step (6) through a reverse osmosis membrane; and step (8): performing biological treatment of discharging a retentate obtained in step (7).

* * * * *